US012635848B2

(12) United States Patent
Lee et al.

(10) Patent No.: US 12,635,848 B2
(45) Date of Patent: May 26, 2026

(54) ENDOSCOPIC DEVICE, CONTROL METHOD AND COMPUTER PROGRAM FOR THE ENDOSCOPIC DEVICE

(71) Applicant: MEDINTECH INC., Seoul (KR)

(72) Inventors: Chi Won Lee, Namyangju-si (KR);
Myung Joon Kim, Gwacheon-si (KR);
Tae Hyeon Kim, Seoul (KR); **Seok Ho
Cho, Seoul (KR); Dong Hyeok Kim**,
Seoul (KR)

(73) Assignee: MEDINTECH INC., Seoul (KR)

( * ) Notice: Subject to any disclaimer, the term of this
patent is extended or adjusted under 35
U.S.C. 154(b) by 203 days.

(21) Appl. No.: 18/585,522

(22) Filed: Feb. 23, 2024

(65) Prior Publication Data

US 2025/0268455 A1 Aug. 28, 2025

(51) Int. Cl.
| | |
|---|---|
| *A61B 1/00* | (2006.01) |
| *A61B 1/015* | (2006.01) |
| *A61B 1/04* | (2006.01) |
| *A61B 1/273* | (2006.01) |
| *G06N 3/08* | (2023.01) |
| *G06V 10/56* | (2022.01) |

(Continued)

(52) U.S. Cl.
CPC .... *A61B 1/000096* (2022.02); *A61B 1/00006*
(2013.01); *A61B 1/000094* (2022.02); *A61B
1/0002* (2013.01); *A61B 1/015* (2013.01);
*A61B 1/04* (2013.01); *G06N 3/08* (2013.01);
*G06V 10/56* (2022.01); *G06V 10/764*
(2022.01); *G06V 10/82* (2022.01); *G06V
20/50* (2022.01); *G16H 40/63* (2018.01); *A61B
1/2733* (2013.01); *G06V 2201/031* (2022.01)

(58) Field of Classification Search
CPC .......... A61B 1/000096; A61B 1/00006; A61B
1/0002; A61B 1/015; A61B 1/04; A61B
1/2733; G06V 10/764; G06V 10/82;
G06V 20/50; G06V 2201/031; G16H
40/63
See application file for complete search history.

(56) References Cited

U.S. PATENT DOCUMENTS

| | | |
|---|---|---|
| 2022/0039806 A1 | 2/2022 | Holmstrom |
| 2022/0046166 A1* | 2/2022 | Holmstrom ............ H04N 23/56 |

(Continued)

FOREIGN PATENT DOCUMENTS

| | | |
|---|---|---|
| JP | 2021-037113 A | 3/2021 |
| KR | 10-2021-0083201 A | 7/2021 |

(Continued)

OTHER PUBLICATIONS

Extended European Search Report received in European Patent
Application No. 24159276.5, dated Aug. 12, 2024 in 25 pages.

(Continued)

*Primary Examiner* — Nasim N Nirjhar
(74) *Attorney, Agent, or Firm* — Harvest IP Law, LLP

(57) ABSTRACT

A control method for an endoscopic device includes obtaining, from an image sensor, an image of an inside of a body, inputting the image to an artificial neural network model trained to classify the obtained image, classifying and outputting, by the artificial neural network model, the image as an air situation image, a water situation image, and/or a suction situation image, and controlling the endoscopic device to drive an air unit, a water unit, and/or a suction unit according to an output classification result.

12 Claims, 8 Drawing Sheets

(51) Int. Cl.

| | | |
|---|---|---|
| *G06V 10/764* | (2022.01) | |
| *G06V 10/82* | (2022.01) | |
| *G06V 20/50* | (2022.01) | |
| *G16H 40/63* | (2018.01) | |

(56) References Cited

U.S. PATENT DOCUMENTS

| | | | |
|---|---|---|---|
| 2022/0189015 A1 | 6/2022 | Guohua | |
| 2023/0222666 A1* | 7/2023 | Takenouchi | G16H 30/40 |
| 2024/0057848 A1 | 2/2024 | Fukatsu et al. | |
| 2024/0057856 A1* | 2/2024 | Abdulqader | A61B 1/000096 |
| 2024/0423443 A1* | 12/2024 | Oneyama | A61B 1/00045 |

FOREIGN PATENT DOCUMENTS

| | | | |
|---|---|---|---|
| KR | 10-2496672 B1 | 2/2023 | |
| KR | 10-2584741 B1 | 10/2023 | |
| KR | 10-2639202 B1 | 2/2024 | |
| WO | WO 2022/234641 A | 11/2022 | |

OTHER PUBLICATIONS

Office Action in corresponding Japanese Application No. 2025-026467 dated Oct. 2, 2025.

* cited by examiner

FIG. 4

A : AIRING LOCATION
B : ESOPHAGUS

ENDOSCOPIC DEVICE, CONTROL METHOD AND COMPUTER PROGRAM FOR THE ENDOSCOPIC DEVICE

TECHNICAL FIELD

The disclosure relates to a control method for an endoscopic device using an artificial neural network model, an endoscopic device, and a computer program.

BACKGROUND ART

An endoscope is a general term for a medical instrument for observing organs by inserting a scope into a body, without surgery or autopsy. Endoscopy involves inserting a scope into a human body, irradiating light, and visualizing light reflected from a surface of an inner wall. There are different types of endoscopes depending on a purpose and body part. Thus, endoscopes may be largely classified into rigid endoscopes in which an endoscope tube is formed of a metal and flexible endoscopes such as gastrointestinal endoscopes.

During an endoscopic treatment, an endoscopist needs to perform operations of pressing an air button when the esophagus is constricted while entering the esophagus, a water button when there is a foreign matter on a screen, and a suction button when gastric juice is shown on the screen or when exiting the esophagus at the end of a procedure. Thus, one endoscopic diagnosis may require pressing many buttons, which may make the entire procedure difficult.

DISCLOSURE

Technical Problem

Provided are a control method for an endoscopic device, an endoscopic device, and a computer program, wherein air, water, and/or suction situations of an endoscope are identified without an operation of a user and airing, watering, and/or sucking up are automatically performed as identified results are transmitted to an endoscopic system.

Additional aspects will be set forth in part in the description which follows and, in part, will be apparent from the description, or may be learned by practice of the presented embodiments of the disclosure.

Technical Solution

According to an aspect of the disclosure, a control method for an endoscopic device including at least one processor, includes obtaining, from an image sensor, an image of an inside of a body, inputting the image to an artificial neural network model trained to classify the obtained image, classifying and outputting, by the artificial neural network model, the image as an air situation image, a water situation image, and/or a suction situation image, and controlling the endoscopic device to drive an air unit, a water unit, and/or a suction unit according to an output classification result.

The artificial neural network model may include a plurality of artificial neural network models, wherein the plurality of artificial neural network models may classify and output the image as at least one situation image from among the air situation image, the water situation image, and/or the suction situation image.

In the classifying and outputting, by the artificial neural network model, of the image as the air situation image, the water situation image, and/or the suction situation image, the artificial neural network model may be trained to determine an image in which an organ is constricted when the endoscopic device enters the body as the air situation image.

In the classifying and outputting, by the artificial neural network model, of the image as the air situation image, the water situation image, and/or the suction situation image, the artificial neural network model may be trained to determine an image in which there is a foreign matter on a lens of the endoscopic device as the water situation image, the air situation image, and/or the suction situation image.

In the classifying and outputting, by the artificial neural network model, of the image as the air situation image, the water situation image, and/or the suction situation image, the artificial neural network model may be trained to determine an image in which the endoscopic device ends a procedure and is extracted from an organ or an image in which a material required to be removed is identified inside an organ as the suction situation image.

The artificial neural network model may include a convolutional neural network (CNN).

The artificial neural network model may include a convolution layer and a fully-connected layer, wherein the convolution layer may extract features of an input image inside the body through a convolution operation, and the fully-connected layer may output a classification result wherein the extracted features of the image finally correspond to a situation image from among the air situation image, the water situation image, and/or the suction situation image.

The classifying and outputting, by the artificial neural network model, of the image as the air situation image, the water situation image, and/or the suction situation image may include applying a thresholding value to the image classified by the artificial neural network model.

The classifying and outputting, by the artificial neural network model, of the image as the air situation image, the water situation image, and/or the suction situation image may include identifying matching degrees with classification results of previous and subsequent images of the classified image.

The classifying and outputting, by the artificial neural network model, of the image as the air situation image, the water situation image, and/or the suction situation image may include labeling the image according to the air situation image, the water situation image, and/or the suction situation image, wherein a labeled label may be a multi-label to which labeling of information about a part of the inside of the body of the image is added.

According to another aspect of the disclosure, an endoscopic device includes a memory storing an image of an inside of a body captured by the endoscopic device, and a processor configured to input the image of the inside of the body to a trained artificial neural network model, classify and output the image as an air situation image, a water situation image, and/or a suction situation image, and control the endoscopic device to drive an air unit, a water unit, and/or a suction unit according to an output classification result.

The processor may be further configured to obtain the image of the inside of the body from an image sensor through an image obtainer.

The processor may be further configured to transmit a control signal of a controller to a driver, wherein the driver may be configured to open or close a valve connected to an air pump of the air unit, open or close a valve connected to a water pump of the water unit, or open or close a valve connected to a suction pump of the suction unit, according to the control signal.

The processor may be further configured to perform postprocessing on the image output by classifying the image as the air situation image, the water situation image, and/or the suction situation image, through a postprocessor.

The postprocessor may include a thresholding value comparator configured to apply a thresholding value to the classified image, and a matching degree identifier configured to identify matching degrees with classification results of previous and subsequent images of the classified image.

According to another aspect of the disclosure, a computer program is stored in a recording medium to execute the method described above by using a computer.

Advantageous Effects

According to embodiments, when an esophagus is constricted, when there is a foreign matter on a screen, when gastric juice is shown on a screen, and when an endoscopic device is extracted from an esophagus after a procedure, an air situation, a water situation, and a suction situation may be automatically classified through an image classification process of an artificial neural network model by using an image obtained through an image sensor, and an air unit, a water unit, and a suction unit may be automatically driven based on classification results, without an operation of a doctor during an endoscopic procedure.

Effects of the disclosure are not limited to those described above.

DESCRIPTION OF DRAWINGS

FIG. 4 is a conceptual diagram showing in detail an endoscopic system according to an embodiment;

MODE FOR INVENTION

Figure 1:
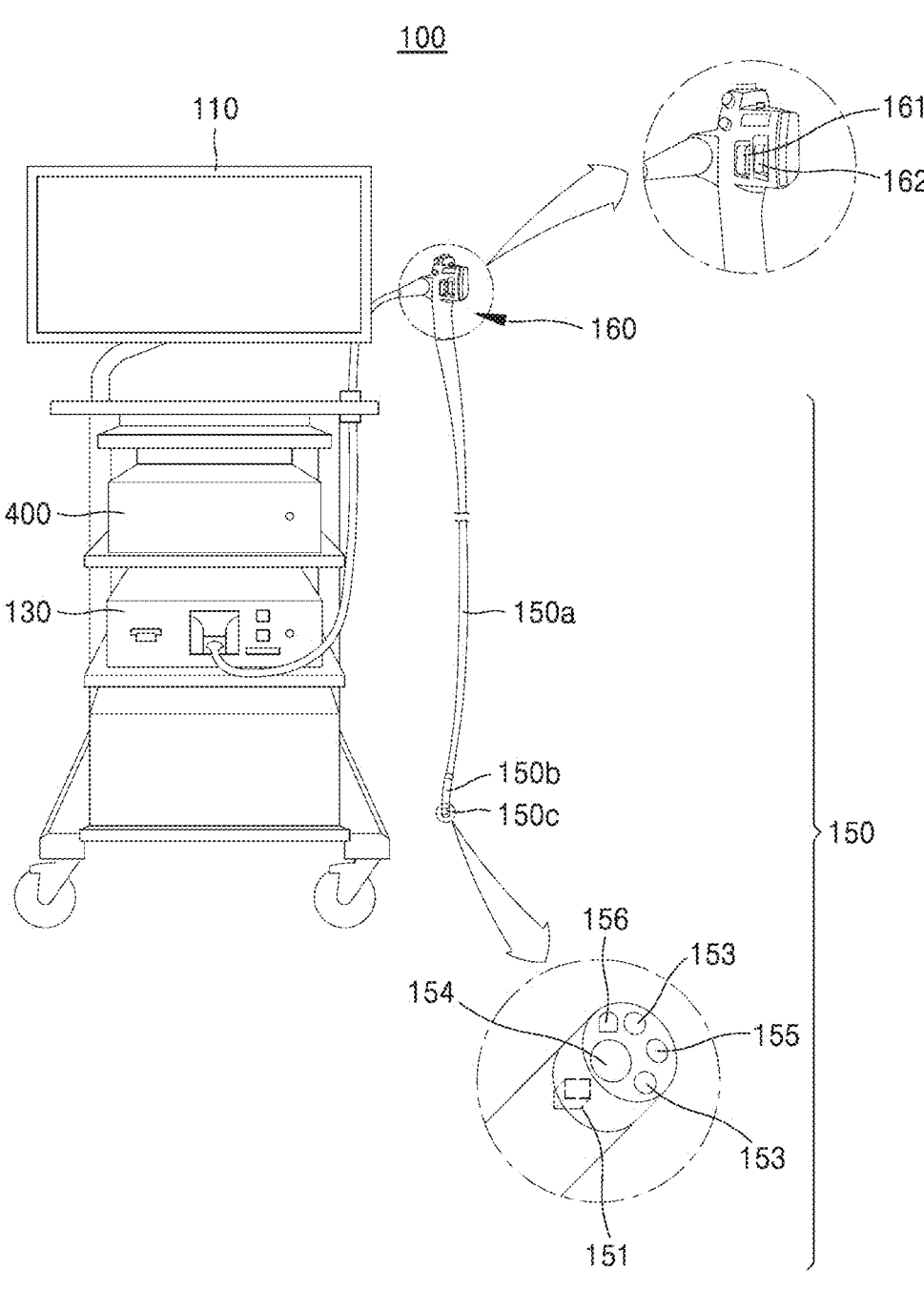
FIG. 1 is a diagram of an endoscopic device according to an embodiment.

Terms used in the disclosure are used only to describe a specific embodiment, and may not be intended to limit the scope of other embodiments. An expression used in the singular may encompass the expression in the plural, unless it has a clearly different meaning in the context. Terms used herein, including technical or scientific terms, may have the same meaning as commonly understood by one of ordinary skill in the art described in the disclosure. Among terms used in the disclosure, terms defined in a general dictionary may be interpreted as having the same or similar meanings as those in the context of the related technology, and unless explicitly defined in the disclosure, the terms are not interpreted in ideal or excessively formal meanings. In some cases, even terms defined in the disclosure cannot be interpreted to exclude embodiments.

Hereinafter, various embodiments will be described in detail with reference to the accompanying drawings such that one of ordinary skill in the art may easily implement the disclosure. However, the technical idea of the disclosure may be implemented by being modified in various forms, and thus is not limited to embodiments described in the present specification. While describing embodiments of the present specification, detailed descriptions about a related well-known technology are omitted when it is determined that describing the well-known technology in detail may blur the gist of the technical idea of the disclosure. Same reference numerals are assigned to same or similar elements, and redundant descriptions thereof are omitted.

As used herein, the term "unit" or "-er/or" denotes a component performing a specific function performed by software or hardware such as a field-programmable gate array (FPGA) or an application-specific integrated circuit (ASIC). However, the "unit" or "-er/or" is not limited by being performed by software or hardware. The "unit" or "-er/or" may be present in the form of data stored in a storage medium capable of being addressed or may be implemented as instructions so that one or more processors perform a specific function.

The software may include a computer program, a code, an instruction, or a combination thereof, and may configure a processing device to operate as desired or instruct the processing device independently or collectively. The software and/or data may be embodied, permanently or temporarily, by any type of machine, component, physical device, virtual equipment, computer storage medium or device, or transmitted signal wave, such as to be analyzed by the processing device or provided to the processing device. The software may be distributed on a computer system connected to a network, and stored or executed in a distributed manner. The software and data may be stored in one or more computer-readable recording media. The software may be read into a main memory from another computer-readable medium, such as a data storage device, or from another device through a communication interface. Software instructions stored in the main memory may enable a processor to perform processes or operations that will be described below in detail. Alternatively, processes matching the principle of the disclosure may be performed by using a fixed wiring circuit instead of or in combination with the software instructions. Accordingly, embodiments matching the principle of the disclosure are not limited to any specific combination of a hardware circuit and software.

Also, the terms used in the present specification are only used to describe specific embodiments, and are not intended to limit the disclosure. An expression used in the singular encompasses the expression in the plural, unless it has a clearly different meaning in the context. In the present specification, it is to be understood that terms such as "including" or "having", etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added. While such terms as "first", "second", etc., may be used to describe various components, such components are not limited to the above terms. The above terms are used only to distinguish one component from another.

A "learning model" stated in the disclosure may include any form of algorithm or methodology used to learn or interpret a specific pattern or structure from data. In other words, the learning model may include not only a machine learning model, such as a regression model, a decision-making tree, a random forest, a support vector machine, a K-nearest neighbor, Naive Bayes, or a clustering algorithm, but also a deep learning model, such as a neural network, a convolution neural network, a recurrent neural network, a transformer-based neural network, a generative adversarial network (GAN), or an autoencoder. The learning model may specify a set of learned parameters or weights that are used to predict or classify an output for a specific input, and the learning model may be trained through a method such as supervised learning, unsupervised learning, semi-supervised learning, or reinforcement learning. In addition, the learning model may include not only a single model but also various learning methods and structures, such as an ensemble model, a multi-modal model, and a model through transfer learning. The learning model may be pre-trained in a computer device separate from a computer device that predicts an output for an input, and used in another computer device.

FIG. 1 is a diagram of an endoscopic device 100 according to an embodiment.

Referring to FIG. 1, the endoscopic device 100 according to an embodiment may be a flexible endoscope, in detail, a gastrointestinal endoscope. The endoscopic device 100 may include a configuration for obtaining a medical image by photographing the inside of digestive organs and a configuration for performing treatment, by inserting a tool when necessary, while viewing the medical image.

The endoscopic device 100 may include an output unit 110, a controller 400, a driver 130, a scope 150, and the controller 400.

The output unit 110 may include a display displaying a medical image. The output unit 110 may include a display module capable of realizing a touch screen or outputting visualized information, such as a liquid crystal display (LCD), a thin-film transistor-liquid crystal display (TFT LCD), an organic light-emitting diode (OLED), a flexible display, or a 3-dimensional (3D) display.

The output unit 110 may include any unit configured to provide information about a medical image, i.e., an image of the inside of a body. For example, the output unit 110 may include a speaker configured to provide audio information about the image of the inside of the body.

The output unit 110 may display the image of the inside of the body, obtained by the scope 150, or the image of the inside of the body, processed by the controller 400. The output unit 110 may display the image of the inside of the body and further display a result of an artificial neural network model classifying and analyzing the image of the inside of the body.

For example, the output unit 110 may display information indicating that a corresponding frame of the image of the inside of the body requires suction, information indicating that suction is being currently performed, or the like.

In FIG. 1, only one output unit 110 is illustrated, but there may be a plurality of the output units 110. In this case, an output unit configured to display the image of the inside of the body, obtained by the scope 150, and an output unit configured to display information processed by the controller 400 may be distinguished from each other. Alternatively, one output unit 110 may be divided into a first screen displaying the image of the inside of the body, obtained by the scope 150, and a second screen displaying the image of the inside of the body and information processed by the controller 400.

The controller 400 may control overall operations of the endoscopic device 100. The controller 400 may include any type of device capable of processing data. For example, the controller 400 may be a data processing device embedded in hardware, which includes a physically structured circuit to perform a function represented by code or command included in a program. Examples of the data processing device embedded in hardware may include processing devices, such as a microprocessor, a central processing unit (CPU), a processor core, a multiprocessor, an application-specific integrated circuit (ASIC), and a field programmable gate array (FPGA), but the scope of the disclosure is not limited thereto.

The controller 400 may control movement of the scope 150 through the driver 130 connected to the scope 150. The controller 400 may perform various control operations for photographing the inside of the body, in particular, the inside of digestive organs, through the scope 150.

The controller 400 may perform various processes on the medical image obtained through the scope 150. The controller 400 may control the endoscopic device 100, based on a control signal received from a computing device. For example, the controller 120 may open or close a suction pump according to an open or close signal of a valve connected to the suction pump.

The driver 130 may provide power required for the scope 150 to be inserted into the body or to move inside the body. For example, the driver 130 may include a plurality of motors connected to a wire inside the scope 150 and a tension adjustor configured to adjust tension of the wire. The driver 130 may control power of each of the plurality of motors to control the scope 150 in various directions.

Meanwhile, in FIG. 1, the controller 400 and the driver 130 are illustrated as separate individual pieces of hardware, but are not limited thereto. For example, the controller 400 and the driver 130 may be included in one piece of hardware or in two or more pieces of hardware. When the controller 400 and the driver 130 are included in two or more pieces of hardware, a portion of a configuration of the controller 400 and a portion of a configuration of the driver 130 may be physically divided.

The scope 150 may include an insertion portion 150a, a curved portion 150b, and a fore-end portion 150c. At least one of an air pump configured to inject air into the body through the scope 150, the suction pump configured to suck up the air from the inside of the body through the scope 150 by providing negative pressure or vacuum, and a water pump configured to inject wash water into the body through the scope 150 may be provided inside the insertion portion 150a, the curved portion 150b, and the fore-end portion 150c. Each pump may include a valve for controlling a flow of fluid. The valve of each pump may be opened or closed by the controller 400.

According to an embodiment, the valve of the suction pump may be opened or closed based on control by the controller 400 or a control signal of the computing device.

According to an embodiment, the controller 400 may open the suction valve, based on a time of opening the suction valve, calculated by the computing device. The controller 400 may block the suction valve after the time calculated by the computing device or based on a suction valve blocking signal of the computing device.

The scope 150 may include the insertion portion 150*a* inserted into the body, in particular, into the digestive organs, and an operator 160 configured to control movement of the insertion portion 150*a* and receive inputs from a user to perform various procedures inside the digestive organs.

The insertion portion 150*a* is configured to be flexibly bendable and has one end connected to the driver 130, and thus, a bending degree or direction may be determined by the driver 130. The image of the inside of the body is captured and the procedure is performed at a distal end of the insertion portion 150*a*, and thus, the scope 150 may include several cables and tubes extending to the distal end of the insertion portion 150*a*.

The curved portion 150*b* and the fore-end portion 150*c* may be provided at a distal end portion of the insertion portion 150*a*. The fore-end portion 150*c* may include an image sensor 151 configured to obtain the image of the inside of the body. The fore-end portion 150*c* has a rotating angle adjusted by the driver 130 that received a control signal of the controller 400, and may identify each part inside the body, capture the image of the inside of the body, and perform a procedure inside the body.

The curved portion 150*b* may be connected to the fore-end portion 150*c*. The driver 130 may adjust curvature of the curved portion 150*b* by receiving a control signal of the controller 400. The rotating angle of the fore-end portion 150*c* may be adjusted according to the curvature of the curved portion 150*c*.

According to the present embodiment, when a first curve steerer 161 and a second curve steerer 162 are driven, a signal is transmitted to the controller 400 through a signal transmitting system mounted on the operator 160. The signal processed by the controller 400 may be transmitted to the driver 130 to drive the motor, thereby controlling the curved portion 150*b*. The first curve steerer 161 controls up and down movements of the curved portion 150*b* and the fore-end portion 150*c*, and the second curve steerer 162 controls left and right movements of the curved portion 150*b* and the fore-end portion 150*c*.

Referring to FIG. 1, the fore-end portion 150*c* of the scope 150 may include the image sensor 151 therein and a light source 153, a lens 154, a first working channel 155, and a second working channel 156 at the end. The image of the inside of the body captured through the lens 154 may be sensed trough the image sensor 151. The light source 153 emits light in an area adjacent to the lens 154 to brighten a dark interior of the body, so that the photographing of the inside of the body through the lens 154 is further clear and precise.

A tool for treating a lesion during an endoscope procedure may be inserted through the first working channel 155. For example, wash water for watering may be supplied into the body through an operator working channel 163, through the first working channel 155. Also, for example, the first working channel 155 may suck up fluid inside the body, in particular, inside the digestive organs, through the valve of the suction pump of a suction unit 430.

In FIG. 1, the second working channel 156 is illustrated in addition to the first working channel 155. The second working channel 156 may perform a different type of operation from an operation performed in the first working channel 155. For example, when the first working channel 155 is performing an operation of sucking up fluid, the second working channel 156 may perform an operation of injecting air for the airing into the body.

The operator 160 may include a plurality of input buttons for providing various functions so that an endoscopist may control steering of the insertion portion 150*a* and perform a procedure through the first working channel 155. The endoscopist may perform suction inside the digestive organs through the operator 160, separately from control by the computing device.

The operations of the controller 400 described above may be performed by the driver 130 and in this regard, the driver 130 may include a necessary processing device, such as a microprocessor, a central processing unit (CPU), or the like. In this case, the controller 400 may process the image of the inside of the body, obtained through the scope 150, and the driver 130 may control the endoscopic device 100, based on the control signal received from the computing device.

Figure 2:
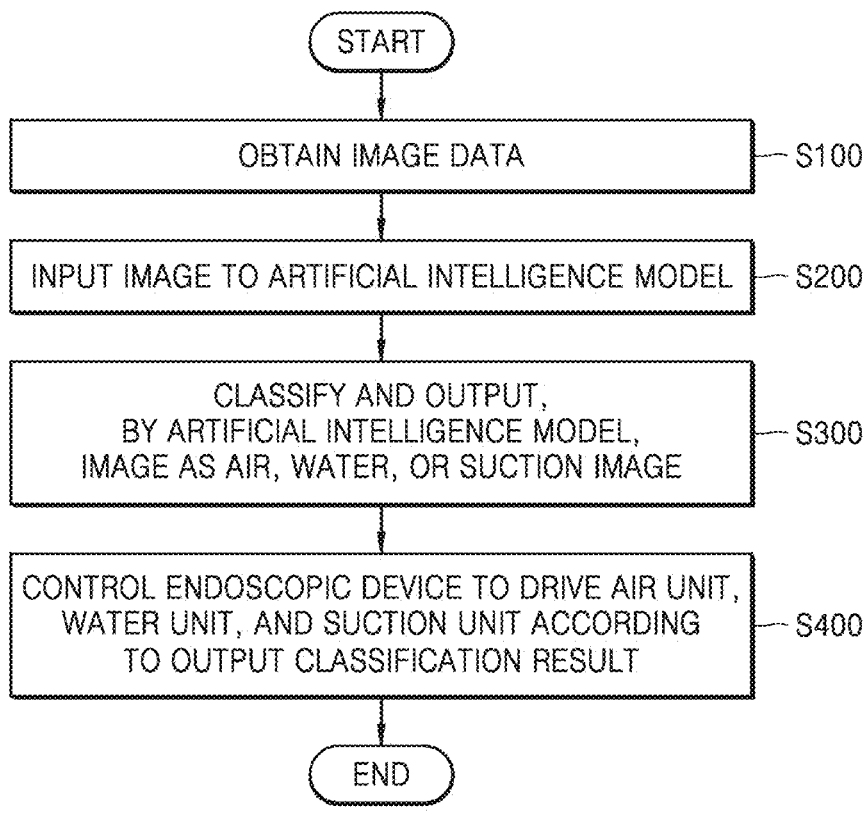
FIG. 2 is a flowchart of a control method for an endoscopic device, according to an embodiment.
Figure 3:
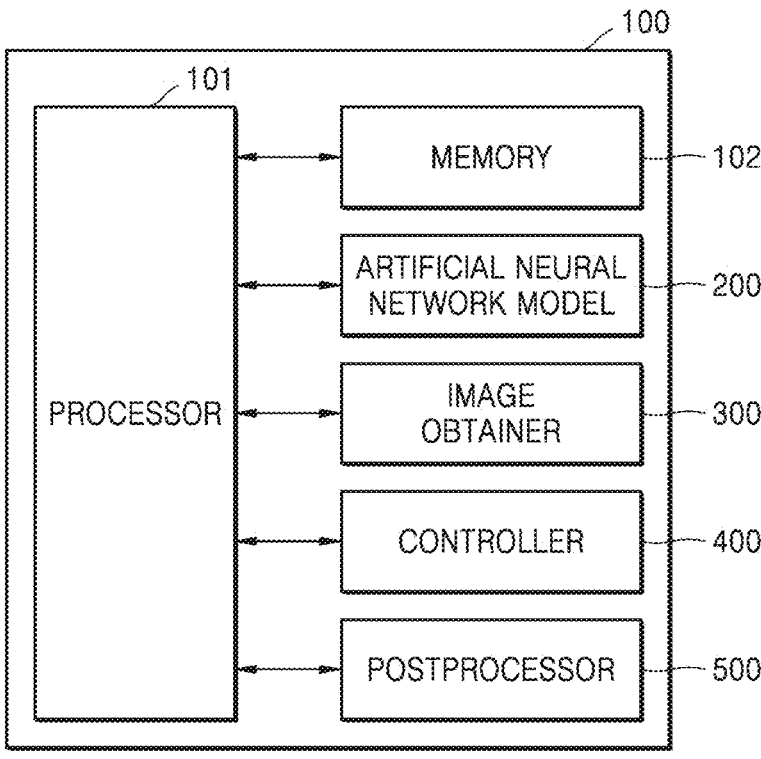
FIG. 3 is a block diagram of an endoscopic system according to an embodiment.
Figure 4:
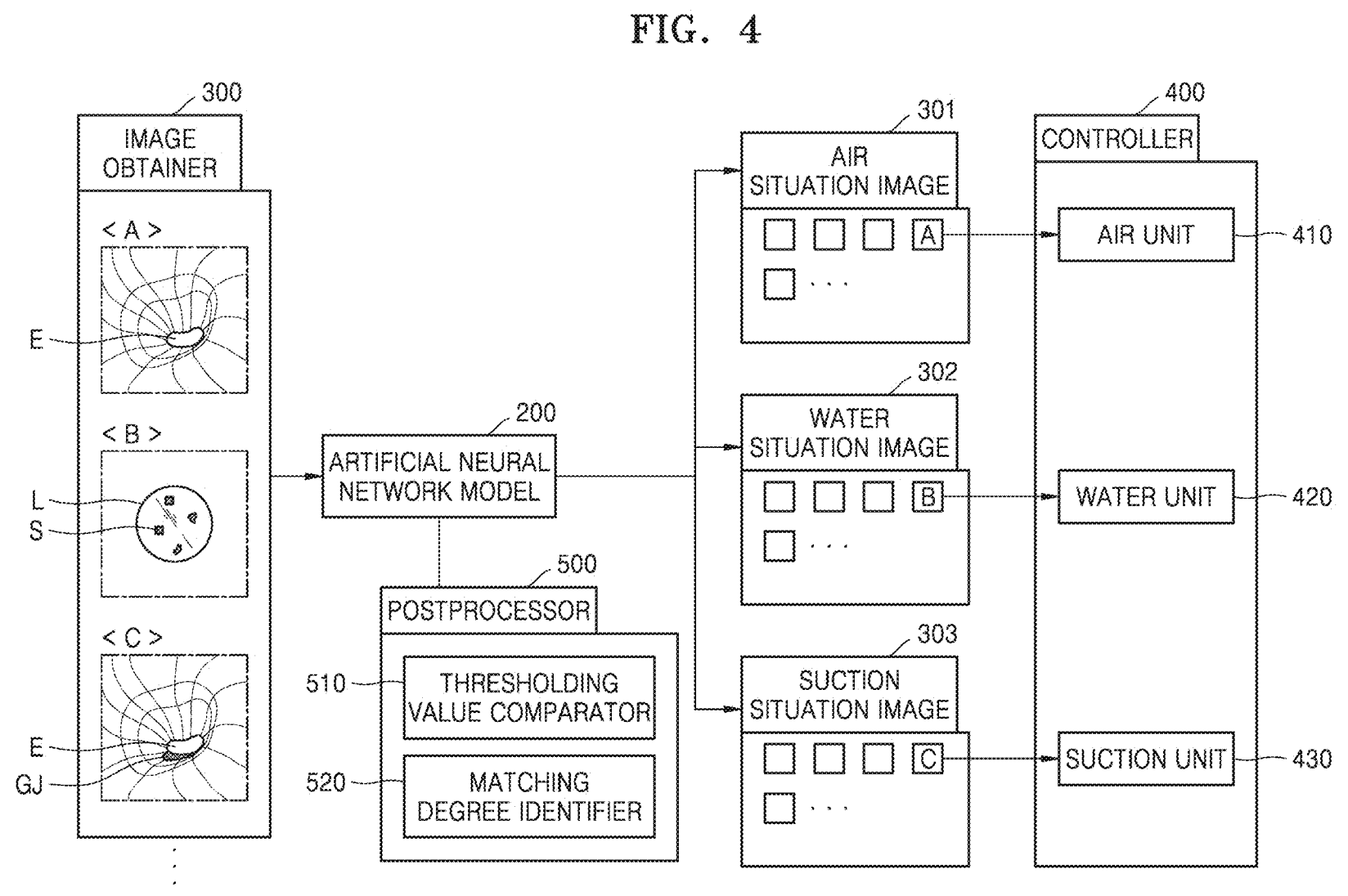

FIG. 2 is a flowchart of a control method for the endoscopic device 100, according to an embodiment. FIG. 3 is a block diagram of an endoscopic system according to an embodiment. FIG. 4 is a conceptual diagram showing in detail an endoscopic system according to an embodiment.

Referring to FIGS. 1 to 4, the control method for the endoscopic device 100, according to an embodiment, includes obtaining the image of the inside of the body from the image sensor 151 (operation S100), inputting the image to an artificial neural network model 200 trained to classify an obtained image (operation S200), the artificial neural network model 200 classifying and outputting the image as an air situation image, a water situation image, and/or a suction situation image (operation S300), and controlling the endoscopic device 100 to drive an air unit 410, a water unit 420, and/or a suction unit 430 according to an output classification result (operation S400).

The endoscopic device 100 according to an embodiment may include a hardware device configured to perform collective processes and operations on data or a portion of the hardware device, and may include a software-based computing environment connected to a communication network. For example, the endoscopic device 100 may include a server that performs intensive data processing functions and shares resources, or may include a client that shares resources through an interaction with the server.

Also, the endoscopic device 100 may include a cloud system enabling a plurality of servers and clients to interact with each other to collectively process data. The above description is only an example related to a configuration of the endoscopic device 100, and thus, the configuration of the endoscopic device 100 may be variously configured within the scope comprehensible by one of ordinary skill in the art, based on the content of the disclosure.

Referring to FIG. 3, the endoscopic device 100 according to an embodiment may include a processor 101, a memory 102, the artificial neural network model 200, an image obtainer 300, the controller 400, and a postprocessor 500.

The processor 101 according to an embodiment may be understood as a configuration unit including hardware and/ or software for performing a computing operation. For example, the processor 101 may perform data processing for machine learning by reading a computer program. The processor 101 may process calculations, such as processing of input data for machine learning, feature extraction for machine learning, and backpropagation-based error calculation. The processor 101 for performing such data processing may include a central processing unit (CPU), a general-purpose graphics processing unit (GPGPU), a tensor processing unit (TPU), an application specific integrated circuit (ASIC), or a field programmable gate array (FPGA). The type of processor 101 described above is only an example and a type of the processor 101 may be variously configured within the scope comprehensible by one of ordinary skill in the art, based on the content of the disclosure.

The processor 101 may train the artificial neural network model 200 by using the image of the inside of the body, e.g., an endoscopic video, as training data. In detail, the processor 101 may train the artificial neural network model 200 to determine, in real time, whether the inside of the body requires airing, watering, and/or suction, based on the endoscopic image obtained by capturing the inside of the body. Here, the endoscopic image may include the endoscopic video.

The image of the inside of the body, i.e., the endoscopic video, may be input to the trained artificial neural network model 200, the image may be classified and output as the air situation image, the water situation image, and/or the suction situation image, and the endoscopic device 100 may be controlled to drive the air unit 410, the water unit 420, and/or the suction unit 430 according to the output classification result.

In the present specification, the inside of the body may refer to organs, such as stomach, duodenum, small intestine, and large intestine, and may specifically refer to parts of the organs, for example, a cardia, a gastric angle, and a pylorus. Hereinafter, the disclosure will be described with an example of digestive organs.

During an endoscopic procedure, an endoscopist needs to perform, when performing an endoscopic treatment, operations of pressing an air button when an esophagus is constricted while entering the esophagus, a water button when there is a foreign matter on the lens 154, and a suction button when gastric juice is shown on the lens 154, i.e., a screen, or when exiting the esophagus at the end of a procedure. Thus, the endoscopist has a difficulty because many buttons need to be pressed during one endoscopic diagnosis.

In detail, when the endoscopic procedure is performed, a distance between the scope 150 including the lens 154 and the digestive organs needs to be secured. Thus, a medical staff may expand organs by injecting the air into the digestive organs during the endoscopic procedure. When air injection is not sufficient, a lesion positioned between wrinkles of an organ or a depressed lesion may not be observed. Also, when an injected amount of the air changes, a shape of an organ is changed and a shape of a lesion is changed accordingly, and thus, adequate air injection determined in real time during an endoscopic procedure is essential for accurate diagnosis. When there is a foreign matter on the lens 154, accuracy of a medical image is decreased, and thus, air may be ejected to the lens 154 to remove the foreign matter.

Also, during the endoscopic procedure, a lesion and an affected area surrounding the lesion may need to be washed, and the lens 154 may need to be washed in case a screen is not well visible due to a foreign matter on the lens 154. In this case, wash water may be ejected to the affected area or the lens 154.

Also, while the endoscopic procedure is performed, a suction operation of sucking up fluid or foreign matter present inside digestive organs and discharging the same to the outside is frequently performed to secure visibility during the endoscopic procedure and accurately detect a lesion. For example, when there is a foreign matter or fluid around an affected area, it is difficult to secure an accurate image, and thus, suction is performed. In addition, suction is performed to remove debris generated when a biopsy is performed for a procedure or tissue analysis. When the air or gas is excessively injected while organs of a target to be observed are expanded, the suction unit 430 may appropriately suck up the air or gas.

As such, airing, watering, and sucking up are required in various situations, and according to an embodiment, the endoscopic device 100 may determine a case where airing, watering, and/or sucking up are required inside the body, based on the image of the inside of the body, and control the air unit 410, the water unit 420, and the suction unit 430 of the endoscopic device 100 when necessary.

For example, the processor 101 may train the artificial neural network model 200 to determine that suction is required when there is a foreign matter around an affected area indicated in the image of the inside of the body or when the inside of the body is over-expanded.

Here, the processor 101 may train one artificial neural network model 200 configured to determine all of a case where the lens 154 capturing the image of the inside of the body is required to be washed, a case where there is a foreign matter around an affected area indicated in the image of the inside of the body, and a case where the inside of the body is over-expanded, or train a plurality of artificial neural network models 200 respectively corresponding to such cases.

The processor 101 may train the artificial neural network model 200 through supervised learning using training data as an input value. Alternatively, the processor 101 may train the artificial neural network model 200 through unsupervised learning of discovering a standard for data recognition by self-learning a type of data required for the data recognition without separate supervision. Alternatively, the processor 101 may train the artificial neural network model 200 through reinforcement learning of using feedback on whether a result of data recognition according to learning is correct.

The artificial neural network model 200 according to the disclosure may include a convolutional neural network (CNN). However, an embodiment is not limited thereto and the artificial neural network model 200 according to the disclosure may include network models, such as a deep neural network (DNN), a recurrent neural network (RNN), a bidirectional recurrent deep neural network (BRDNN), multilayer perception (MLP), or transformer.

The processor 101 may input the image of the inside of the body to the artificial neural network model 200 that is trained and determine cases where airing, watering, and sucking up are required inside the digestive organs, from the image of the inside of the body. The processor 101 may generate a signal for controlling the endoscopic device 100, based on an output value of the artificial neural network model 200.

In detail, the processor 101 may generate a control signal for performing airing, watering, and/or sucking up. The processor 101 may generate a control signal of selectively opening and closing each valve of the air, water, and/or suction pumps connected to the working channels 155 and 156 to perform suction through the working channels 155 and 156 of the scope 150 of the endoscopic device 100, which is inserted into the digestive organs. The processor 101 may directly generate a control signal for controlling the endoscopic device 100 or instruct the endoscopic device 100 to generate a control signal, based on an output result of the artificial neural network model 200.

For example, the processor 101 may control the valve of the suction pump of the endoscopic device 100 by distinguishing a case where the lens 154 capturing the image of the inside of the body needs to be washed, a case where there is a foreign matter around an affected area indicated in the image of the inside of the body, and a case where the inside of the digestive organs is excessively expanded.

While the endoscopic procedure is performed, the processor 101 may receive the image of the inside of the body in units of frames and determine whether airing, watering, and/or sucking up are required for each frame. The above-described operations may be performed until the endoscopic procedure is ended.

The memory 102 according to an embodiment may be understood as a configuration unit including hardware and/ or software for storing and managing data processed by the endoscopic device 100. In other words, the memory 102 may store any type of data generated or determined by the processor 101 and any type of data received by a network unit (not shown). For example, the memory 102 may include at least one type of storage medium among a flash memory type, a hard disk type, a multimedia card micro type, a card type memory (for example, a secure digital (SD) or an extreme digital (XD) memory), a random access memory (RAM), a static RAM (SRAM), a read-only memory (ROM), an electrically erasable programmable ROM (EE-PROM), a programmable ROM (PROM), a magnetic memory, a magnetic disk, and an optical disk. Also, the memory 102 may include a database system configured to control and manage data by using a certain system. The type of memory 102 described above is only an example and a type of the memory 102 may be variously configured within the scope comprehensible by one of ordinary skill in the art, based on the content of the disclosure.

The memory 102 may structure, organize, and manage data required for the processor 101 to perform operations, a combination of the data, and program code executable by the processor 101. Also, the memory 102 may store program code for operating the processor 101 to generate training data.

According to the disclosure, the memory 102 may store the image of the inside of the body captured by the endoscopic device 100 and store a control signal generated by the processor 101 based on the image.

The network unit according to an embodiment may be understood as a configuration unit that transmits or receives data through any type of well-known wired or wireless communication system. For example, the network unit may perform data transmission or reception by using a wired or wireless communication system, such as a local area network (LAN), a wideband code division multiple access (WCDMA), long-term evolution (LTE), wireless broadband Internet (WiBro), 5th generation (5G) mobile communication, ultra wide-band, ZigBee, radio frequency (RF) communication, wireless LAN, wireless fidelity (Wi-Fi), near field communication (NFC), or Bluetooth. The above-described communication systems are only examples and the wired or wireless communication system for data transmission or reception of the network unit may variously applied in addition to the above examples.

The network unit may receive data required for the processor 101 to perform operations, through wired or wireless communication with any system or any client. Also, the network unit may transmit data generated through operations of the processor 101, through wired or wireless communication with any system or any client. For example, the network unit may receive a medical image by communicating with a medical image storage transmission system, a cloud server configured to perform an operation such as medical data standardization, or a separate computing device. The network unit may transmit various types of data generated through operations of the processor 101 by communicating with the above system, server, or separate computing device.

The processor 101 may input the image of the inside of the body to the trained artificial neural network model 200, classify and output the image as the air situation image, the water situation image, and/or the suction situation image, and control the endoscopic device 100 to drive the air unit 410, the water unit 420, and/or the suction unit 430 according to the output classification result.

The processor 101 may obtain the image of the inside of the body from the image sensor 151 through the image obtainer 300. The processor 101 may transmit a control signal of the controller 400 to the driver 130, and the driver 130 may open or close a valve connected to the air pump of the air unit 410, open or close a valve connected to the water pump of the water unit 420, or open or close a valve connected to the suction pump of the suction unit 430, according to the control signal. The air unit 410, the water unit 420, and the suction unit 430 may be arranged inside the insertion portion 150a of the scope 150 so as to transmit air or supply water towards the inside of the body or suck up air from the inside of the body, based on operation information controlled by the controller 400.

The processor 101 may perform postprocessing on the image output by classifying the image as the air situation image, the water situation image, and/or the suction situation image, through the postprocessor 500.

According to an embodiment, the postprocessor 500 may include, as described below, a thresholding value comparator 510 configured to apply a thresholding value to a classified image and a matching degree identifier 520 configured to identify matching degrees with classification results of previous and subsequent images of the classified image.

Referring to FIG. 4, the image obtainer 300 may obtain the image of the inside of the body. For example, situation images, such as an image A of entering a constricted esophagus E, an image B of a foreign matter S on a lens L, and an image C showing gastric juice GJ around the esophagus E.

Images obtained through the image obtainer 300 as such may be input to the artificial neural network model 200. The artificial neural network model 200 may classify the input several image of the inside of the body as an air situation image 301, a water situation image 302, and/or a suction situation image 303. An image that does not correspond to the above three situation images may be separately classified.

The artificial neural network model 200 may output the three situation images. The output images may be transmitted to one of the air unit 410, the water unit 420, and the suction unit 430 of the controller 400. An image that does not correspond to the above three situation images may not be transmitted to the controller 400.

For example, it may be assumed that the endoscopic device 100 located inside the body has captured a specific image at a specific time. Here, when the image sensor 151 of the endoscopic device 100 located inside the body detects the image A of entering the constricted esophagus E, the image obtainer 300 may obtain the image A of entering the constricted esophagus E, through the image sensor 151. The image A of entering the esophagus E, obtained by the image obtainer 300, may be input to the artificial neural network model 200, and the artificial neural network model 200 may determine that the image A is the air situation image 301, based on trained content.

When the image A is determined as the air situation image 301, the artificial neural network model 200 may output, to the controller 400, information indicating that the image A is the air situation image 301. The controller 400 may open or close the valve connected to the air pump of the air unit 410 through the driver 130, based on the information received from the artificial neural network model 200. The air unit 410 may eject air supplied from the air pump to through the working channels 155 and 156, and the esophagus E is widened as the air is ejected to the constricted esophagus E, and thus, the fore-end portion 150c of the endoscopic device 100 may be easily inserted into the esophagus E.

According to an embodiment, in operation S300 in which the artificial neural network model 200 classifies and outputs the image as the air situation image, the water situation image, and/or the suction situation image, the artificial neural network model 200 may be trained to determine an image in which organs are constricted when the endoscopic device 100 enters the body as the air situation image.

For example, the artificial neural network model 200 may be trained to determine an image in which an esophagus is constricted when the endoscopic device 100 enters the esophagus as the air situation image.

According to an embodiment, in operation S300 in which the artificial neural network model 200 classifies and outputs the image as the air situation image, the water situation image, and/or the suction situation image, the artificial neural network model 200 may be trained to determine an image in which there is a foreign matter on a lens as the air situation image, the water situation image, and/or the suction situation image.

The foreign matter on the lens may be removed by performing at least one operation from among airing, watering, and/or sucking up, so as to remove the foreign matter on the lens.

According to an embodiment, in operation S300 in which the artificial neural network model 200 classifies and outputs the image as the air situation image, the water situation image, and/or the suction situation image, the artificial neural network model 200 may be trained to determine an image in which the endoscopic device 100 completes a procedure and is extracted from organs or an image in which a foreign matter inside an organ is identified as the suction situation image.

For example, the artificial neural network model 200 may be trained to determine an image in which the endoscopic device 100 completes a procedure and is extracted from an esophagus as the suction situation image. In addition, the artificial neural network model 200 may be trained to determine an image in which the endoscopic device 100 identifies a foreign matter inside an organ as the suction situation image, so as to suck up and remove a material required to be removed from inside the organ through suction when the material required to be removed, generated due to extra gastric juice in organs, a digestive matter, nasal discharge, or a lesion, is identified.

In FIG. 4, one artificial neural network model 200 determines whether airing, watering, and/or sucking up are required for various cases, but the artificial neural network model 200 may include a plurality of artificial neural network models configured to determine the cases, respectively.

As such, through airing, watering, and/or sucking up execution solutions automated according to situations by using the artificial neural network model 200 according to the disclosure, physical burden applied to an endoscopist may be dramatically reduced and convenience of endoscopic diagnosis may be significantly improved compared to the prior art in which airing, watering, and/or sucking up are performed through complex operations.

Figure 5:
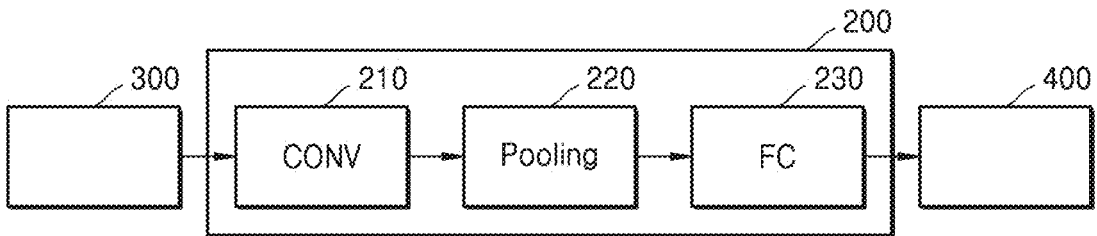
FIG. 5 is a conceptual diagram showing an artificial neural network model according to an embodiment.

FIG. 5 is a conceptual diagram showing the artificial neural network model 200 according to an embodiment.

Referring to FIG. 5, the artificial neural network model 200 according to an embodiment may include a CNN. Images received from the image obtainer 300 may be input to the artificial neural network model 200. In this case, a convolution layer 210 of the artificial neural network model 200 may analyze an image through a convolution operation. The convolution layer 210 may extract features of images by calculating several layers. The extracted features may reduce dimensions of image data through a pooling layer 220, thereby enhancing calculation efficiency of a neural network. The convolution layer 210 and the pooling layer 220 may be iteratively configured to specify the features of the images.

The features extracted through the above processes may be transmitted to a fully-connected (FC) layer 230. The FC layer 230 may use the extracted features inputted to output a classification result wherein each image finally corresponds to a class (an air situation image, a water situation image, or a suction situation image). The output classification result may be transmitted to the controller 400.

Figure 6A:
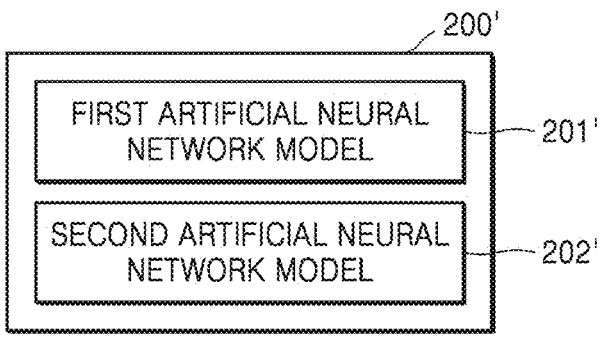
FIGS. 6A and 6B are conceptual diagrams showing artificial neural network models according to other embodiments.
Figure 6B:
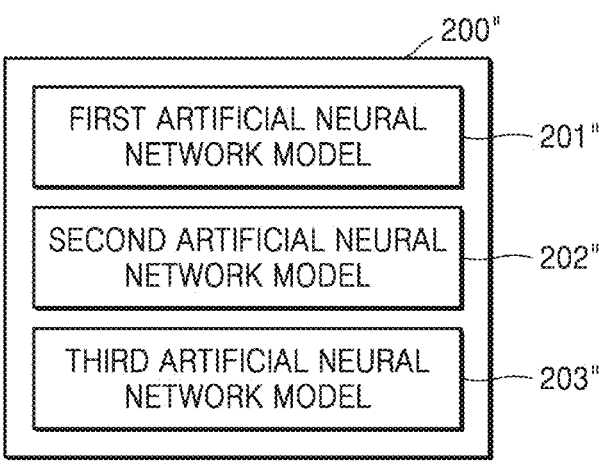

FIGS. 6A and 6B are conceptual diagrams showing artificial neural network models 200' and 200" according to other embodiments. FIG. 6A is a conceptual diagram showing the artificial neural network model 200' according to another embodiment. FIG. 6B is a conceptual diagram showing the artificial neural network model 200" according to another embodiment.

Referring to FIG. 6A, the artificial neural network model 200' may include a plurality of artificial neural network models 201' and 202'. The artificial neural network models 201' and 202' may classify and output an image as at least one situation image from among the air situation image, the water situation image, and/or the suction situation image.

For example, the first artificial neural network model 201' may classify and output an input image as the air situation image and the water situation image, and the second artificial neural network model 202' may classify and output an input image as the suction situation image.

Referring to FIG. 6B, the artificial neural network model 200" may include a plurality of artificial neural network models 201", 202", and 203". The artificial neural network models 201", 202", and 203" may classify and output an image as at least one situation image from among the air situation image, the water situation image, and/or the suction situation image.

For example, the first artificial neural network model 201" may classify and output an input image as the air situation image, the second artificial neural network model 202" may classify and output an input image as the water situation image, and the third artificial neural network model 203" may classify and output an input image as a suction situation image.

A plurality of artificial neural network models according to the disclosure are not limited to those shown in FIGS. 6A and 6B, and the number of artificial neural network models and the range of situation images classified by each artificial neural network model may vary.

Figure 7:
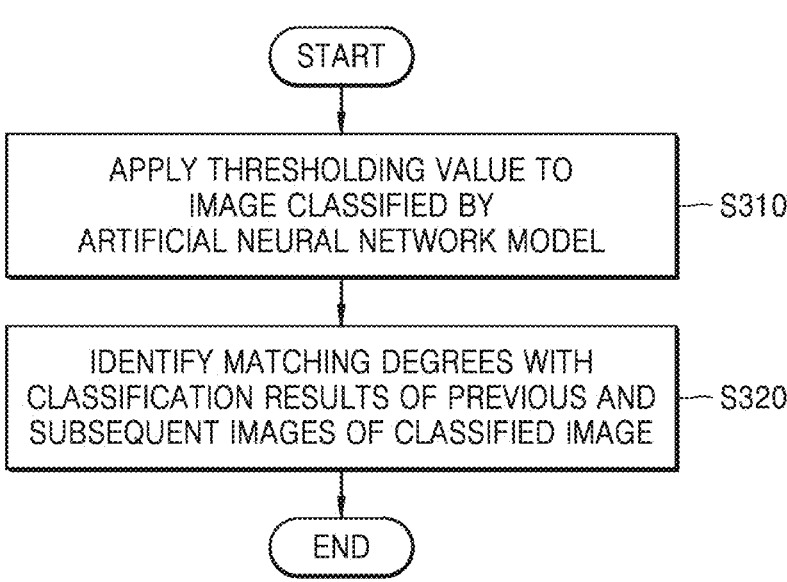
FIG. 7 is a flowchart of detailed operations by which an artificial neural network model classifies and outputs an image as an air, water, or suction situation image in a control method for an endoscopic device, according to an embodiment.

FIG. 7 is a flowchart of detailed operations by which the artificial neural network model 200 classifies and outputs an image as the air, water, or suction situation image in the control method for the endoscopic device 100, according to an embodiment.

Referring to FIG. 7, in operation S300 in which the artificial neural network model 200 classifies and outputs the image as the air situation image, the water situation image, and/or the suction situation image according to the control method for the endoscopic device 100, according to an embodiment, may include applying a thresholding value to the image classified by the artificial neural network model 200 (operation S310) and identifying matching degrees with classification results of previous and subsequent images of the classified image (operation S320).

Figure 8:
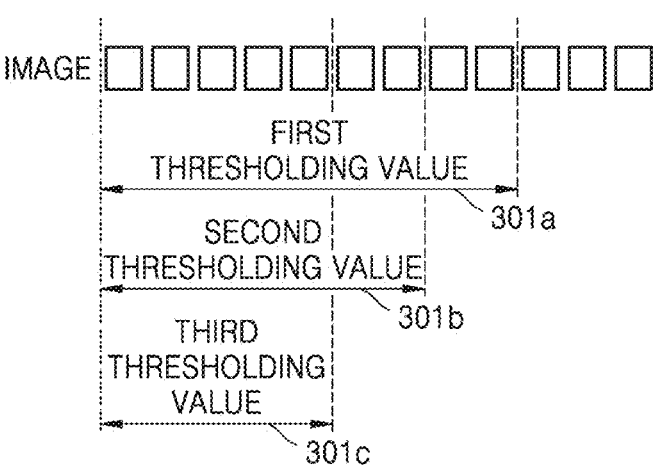
FIG. 8 is a conceptual diagram for describing applying of a thresholding value to an image classified by an artificial neural network model, according to an embodiment.

FIG. 8 is a conceptual diagram for describing the applying of the thresholding value to the image classified by the artificial neural network model 200, according to an embodiment.

Referring to FIG. 8, the thresholding value may be applied as postprocessing for enhancing classification accuracy of the air situation image, the water situation image, and/or the suction situation image, which are determined by using the artificial neural network model 200. Here, it may be determined that only an image satisfying the thresholding value corresponds to a specific situation image, by applying the thresholding value for a specific standard to a classification determination criterion of the air situation image, the water situation image, and/or the suction situation image classified through the artificial neural network model 200.

The thresholding value may be determined based on data learned by using the air situation image, the water situation image, and/or the suction situation image. Also, as shown in FIG. 7, the thresholding value according to classification may be variously set to a first thresholding value 301a, a second thresholding value 301b, or a third thresholding value 301c, so that airing, watering, and sucking up may be differently controlled according to situations by applying different thresholding values depending on a condition of a patient during the endoscopic procedure.

Figure 9:
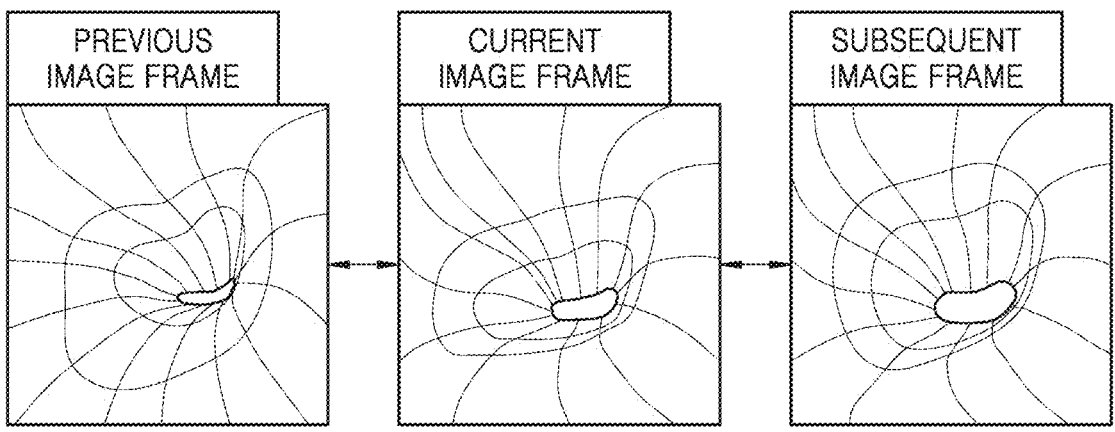
FIG. 9 is a conceptual diagram for describing identifying of matching degrees of classification results of previous and subsequent images of a classified image, according to an embodiment.

FIG. 9 is a conceptual diagram for describing the identifying of the matching degrees of the classification results of the previous and subsequent images of the classified image, according to an embodiment.

Referring to FIG. 9, the matching degrees may be identified as the postprocessing for enhancing the classification accuracy of the air situation image, the water situation image, and/or the suction situation image, which are determined by using the artificial neural network model 200. In other words, the capturing of the image of the inside of the body by the endoscopic device 100 is performed in units of frames, and output matching degrees between images may be identified by comparing an image captured from a previous image frame captured immediately before a frame being currently captured and an image captured from a subsequent image frame captured immediately after the frame being currently captured, with an image of the frame being currently captured. At this time, the output matching degree may improve the classification accuracy of the images classified through the artificial neural network model 200 by checking a matching degree of adjacent frame images for images output after the images corresponding to each frame are input to the artificial neural network model 200 and classified.

Figure 10:
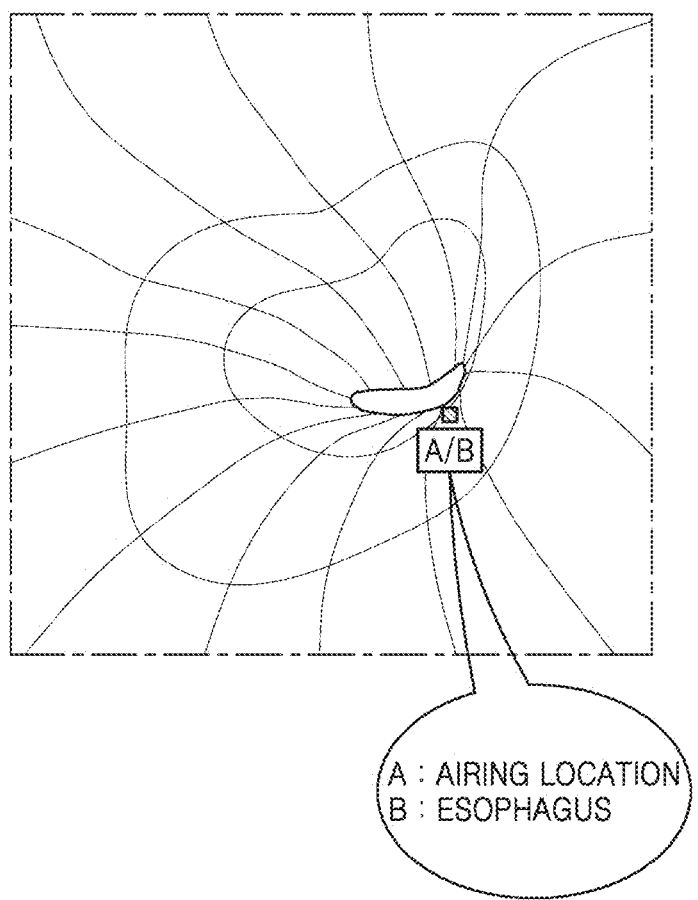
FIG. 10 is a conceptual diagram for describing displaying of a multi-label on a screen of an endoscopic device, according to an embodiment.

FIG. 10 is a conceptual diagram for describing displaying of a multi-label on a screen of the endoscopic device 100, according to an embodiment.

The artificial neural network model 200 may receive a label of an endoscopic video as training data. The endoscopic video may be captured through the endoscopic device 100. The label may include information indicating a state in which a corresponding image of the inside of the body requires airing, watering, and/or sucking up. For example, a state in which sucking up is required may include various states, such as a case where there is a foreign matter around an affected area indicated in the image of the inside of the body and a case where the inside of digestive organs are over-expanded, and in this case, the image of the inside of the body may be labeled as the state in which sucking up is required.

Also, for example, in a case where focus of the image of the inside of the body is clear or in a case where there is no foreign matter around the affected area indicated in the image of the inside of the body, the image of the inside of the body may be labeled as a normal state that does not require sucking up. Labeling may be performed by a medical staff or a separate artificial neural network model for labeling may be used.

According to an embodiment, operation S300 in which the artificial neural network model 200 classifies and outputs the image as the air situation image, the water situation image, and/or the suction situation image may further include labeling each of the air situation image, the water situation image, and/or the suction situation image (operation S330). Here, a labeled label may be a multi-label to which labeling of information about a part of the inside of the body of the image is added.

FIG. 10 illustrates an example of an image of the multi-label. When labeling a specific part of the inside of the body as shown in FIG. 9, in addition to labeling information about airing, watering, or sucking up, information about a corresponding location, for example, an esophagus, duodenum, or stomach, may be additionally indicated on the label and output. In other words, the artificial neural network model 200 may additionally classify and determine at which location inside the body is a water situation, an air situation, and a suction situation, during image classification, and transmit corresponding information to the controller 400.

The controller 400 may also determine information about where the fore-end portion 150c of the endoscopic device 100 is currently located inside an organ of a body and information about whether the fore-end portion 150c is being currently inserted into or extracted from the inside of the body. Accordingly, while controlling the airing, watering, and sucking up of the endoscopic device 100, an air degree, a water degree, and a suction degree may be further precisely controlled according to the location and proceeding direction of the fore-end portion 150c.

The memory 102 may store a plurality of application programs to be operated, and pieces of data and instructions for operations of the computing device. The memory 102 may be implemented as an internal memory, such as ROM or RAM, included in the processor 101, or may be implemented as a memory separate from the processor 101. The memory 102 according to an embodiment may store a neural network and training data.

In detail, the processor 101 may control operations of the computing device by using various programs stored in the memory 102 of the computing device. The processor 101 may include CPU, RAM, ROM, and a system bus. The processor 101 may be implemented as a single CPU or a plurality of CPUs (or a digital signal processor (DSP) or a system-on-chip (SoC)). According to an embodiment, the processor 101 may be implemented as a DSP for processing a digital signal, a microprocessor, or a time controller (TCON). However, the processor 101 is not limited thereto, and may include one or more of a CPU, a micro controller unit (MCU), a micro processing unit (MPU), a controller, an application processor (AP), a communication processor (CP), and an ARM processor, or may be defined by such terms. Also, the processor 101 may be implemented as an SoC, in which a processing algorithm is embedded, or large scale integration (LSI), or may be implemented in the form of FPGA.

The apparatus described above may be realized by a hardware component, a software component, and/or a combination of a hardware component and a software component. For example, the apparatus and component described in embodiments may be realized by using one or more general-purpose computers or special purpose computers, such as a processor, a controller, an arithmetic logic unit (ALU), a digital signal processor, a micro-computer, a field programmable gate array (FPGA), a programmable logic unit (PLU), a micro-processor, or any other device capable of executing and responding to an instruction. A processing device may execute an operating system (OS) and one or more software applications executed on the OS. Also, the processing device may access, store, manipulate, process, and generate data in response to execution of software. For convenience of description, it has been described that one processing device is used, but it would be obvious to one of ordinary skill in the art that the processing device may include a plurality of processing elements and/or a plurality of types of processing elements. For example, the processing device may include a plurality of processors or one processor and one controller. Also, another processing configuration, such as a parallel processor, is possible.

The software may include a computer program, a code, an instruction, or a combination thereof, and may configure the processing device to operate as desired or instruct the processing device independently or collectively. The software and/or data may be embodied, permanently or temporarily, by any type of machine, component, physical device, virtual equipment, computer storage medium or device, or transmitted signal wave, such as to be analyzed by the processing device or provided to the processing device. The software may be distributed on a computer system connected to a network, and stored or executed in a distributed manner. The software and data may be stored in one or more computer-readable recording media.

Methods according to embodiments may be recorded on a computer-readable recording medium by being implemented in the form of program commands executed by using various computers. The computer-readable recording medium may include at least one of a program command, a data file, or a data structure. The program commands recorded in the computer-readable recording medium may be specially designed for an embodiment or well known to one of ordinary skill in the computer software field. Examples of the computer-readable recording medium include magnetic media such as hard disks, floppy disks, and magnetic tapes, optical media such as CD-ROMs and DVDs, magneto-optical media such as floptical disks, and hardware devices specially configured to store and perform program commands, such as read-only memory (ROM), random-access memory (RAM), and flash memory. Examples of the computer command include machine codes generated by a compiler, and high-level language codes executable by a computer by using an interpreter. The hardware device may be configured to operate as one or more software modules to perform operations of an embodiment, or vice versa.

Although the embodiments have been described above with limited examples and drawings, various modifications and changes may be made by one of ordinary skill in the art from the above description. For example, appropriate results may be achieved even if the described technologies are performed in a different order than the described method and/or the components of the described system, structure, device, circuit, etc. are combined or associated in a different form than the described method or replaced or substituted by other components or equivalents.

Therefore, other implementations, other embodiments, and equivalents of claims also fall within the scope of the claims described below.

Explanation of Reference Numerals

100: Endoscopic Device
110: Output Unit
400: Controller
130: Driver
150: Scope
151: Image Sensor
153: Light Source
154: Lens
155, 156: Working Channel
101: Processor
102: Memory
200: Artificial Neural Network Model
300: Image Obtainer
400: Controller
500: Postprocessor

The invention claimed is:

1. A control method for an endoscopic device comprising at least one processor, the control method comprising:
obtaining, from an image sensor, an image of an inside of a body;
inputting the image to an artificial neural network model configured to classify, for each frame, the image of the inside of the body as at least one of an air situation image, a water situation image, or a suction situation image;
performing post-classification processing comprising:
(i) applying a classification-specific threshold to the classified image, and
(ii) determining a matching degree with classification results of a previous frame and a subsequent frame of the classified image; and
controlling the endoscopic device to automatically open or close a corresponding valve of at least one of an air unit, a water unit, or a suction unit of the endoscopic device in response to the classification satisfying the classification-specific threshold and the matching degree exceeding a criterion, thereby executing at least one of airing, watering, or suction through a working channel of the endoscopic device,
wherein the post-classification processing is configured to enhance a classification accuracy of at least one of the air situation image, the water situation image, or the suction situation image, and
wherein the classification-specific threshold is variously set to a first threshold value, a second threshold value, or a third threshold value, so that airing, watering, and sucking up are differently controlled according to situations by applying different threshold values depending on a condition of a patient during an endoscopic procedure.

2. The control method of claim 1, wherein the artificial neural network model comprises a plurality of artificial neural network models, and wherein the plurality of artificial neural network models classify and output the image as at least one situation image from among the air situation image, the water situation image, and/or the suction situation image.

3. The control method of claim 1, wherein the artificial neural network model is trained to determine an image in which an organ is constricted when the endoscopic device enters the body as the air situation image.

4. The control method of claim 1, wherein the artificial neural network model is trained to determine an image in which there is a foreign matter on a lens of the endoscopic device as the water situation image, the air situation image, and/or the suction situation image.

5. The control method of claim 1, wherein the artificial neural network model is trained to determine an image in which the endoscopic device ends a procedure and is extracted from an organ or an image in which a material required to be removed is identified inside an organ as the suction situation image.

6. The control method of claim 1, wherein the artificial neural network model comprises a convolutional neural network (CNN).

7. The control method of claim 6, wherein the artificial neural network model comprises a convolution layer and a fully-connected layer, wherein the convolution layer extracts features of an input image inside the body through a convolution operation, wherein the fully-connected layer outputs a classification result, and wherein the extracted features of the input image finally correspond to a situation image from among the air situation image, the water situation image, and/or the suction situation image.

8. The control method of claim 1, further comprising labeling the image according to the air situation image, the water situation image, and/or the suction situation image, wherein a labeled label is a multi-label to which labeling of information about a part of the inside of the body of the image is added.

9. An endoscopic device comprising:

a memory storing an image of an inside of a body captured by the endoscopic device; and a processor configured to:

input the image of the inside of the body to a trained artificial neural network model, classify, for each frame, the image of the inside of the body as at least one of an air situation image, a water situation image, or a suction situation image, perform post-classification processing comprising:

(i) applying a classification-specific threshold to the classified image, and (ii) determining a matching degree with classification results of a previous frame and a subsequent frame of the classified image; and control, via a driver, at least one of an air unit, a water unit, or a suction unit by automatically opening or closing a corresponding valve in response to the classification satisfying the classification-specific threshold and the matching degree exceeding a criterion, so as to execute at least one of airing, watering, or suction through a working channel of the endoscopic device, wherein the post-classification processing is configured to enhance a classification accuracy of at least one of the air situation image, the water situation image, or the suction situation image, and wherein the classification-specific threshold is configured to be variously set to a first threshold value, a second threshold value, or a third threshold value, so that airing, watering, and sucking up are differently controlled according to situations by applying different threshold values depending on a condition of a patient during an endoscopic procedure.

10. The endoscopic device of claim 9, wherein the processor is further configured to obtain the image of the inside of the body from an image sensor through an image obtainer.

11. A computer program stored in a recording medium to execute the method of claim 1 by using a computer.

12. The method of claim 1, wherein the post-classification processing further comprises, when the classification-specific threshold applied to the classified image is not satisfied or the matching degree identified between adjacent frames is insufficient, temporarily blocking actuation of at least one of the air valve, water valve, or suction valve until a subsequent frame satisfies both the classification-specific threshold and the matching degree.

* * * * *